United States Patent [19]

Brugger

[11] 3,974,378

[45] Aug. 10, 1976

[54] INSPECTION SYSTEM FOR REFLECTIVE AND TRANSPARENT ARTICLES

[76] Inventor: Richard D. Brugger, 4818 Walker Blvd., Erie, Pa. 16509

[22] Filed: Mar. 8, 1974

[21] Appl. No.: 449,381

Related U.S. Application Data

[63] Continuation of Ser. No. 213,999, Dec. 30, 1971, abandoned.

[52] U.S. Cl. .......................... 250/223 B; 250/227; 356/198; 356/240
[51] Int. Cl.² ........................................ G01D 21/04
[58] Field of Search ............... 250/223 B, 227, 562, 250/563; 356/239, 240, 198; 350/190

[56] References Cited
UNITED STATES PATENTS

| | | | |
|---|---|---|---|
| 3,062,964 | 11/1962 | Lubin............................. | 350/190 X |
| 3,150,266 | 9/1964 | Mathias....................... | 250/223 B X |
| 3,292,785 | 12/1966 | Calhoun........................ | 356/240 X |
| 3,321,637 | 5/1967 | Beltz et al........................... | 250/557 |
| 3,328,593 | 6/1967 | Johnson et al. ................ | 250/223 B |
| 3,386,579 | 6/1968 | Schulze et al.................... | 356/198 X |
| 3,571,796 | 3/1971 | Brugger ............................. | 250/227 |
| 3,588,258 | 6/1971 | Sendt................................... | 356/240 |
| 3,639,067 | 2/1972 | Stephens...................... | 250/223 B X |
| 3,687,559 | 8/1972 | Fischer et al................ | 250/223 B X |
| 3,739,184 | 6/1973 | Katsumata et al................. | 356/240 |

*Primary Examiner*—David C. Nelms

[57] ABSTRACT

A means of optically recognizing the presence of substances on or within the walls of a transparent object or on the surface of a reflecting object by impinging a bar of light on the object and collecting the reflected or refracted rays of light by means of optical fibers and directing the light onto a photosensitive element connected to a circuit for using said information. The device disclosed is particularly suitable for inspecting glass jars to detect the presence of foreign material on the surface of the jars, such as "doping" or a mold release compound during manufacture, such as black spots which are undesirable because they have an unsightly appearance. The mold release is a necessary part of the jar manufacture process. The present system involves manual inspection of jars.

5 Claims, 11 Drawing Figures

Inventor

RICHARD D. BRUGGER

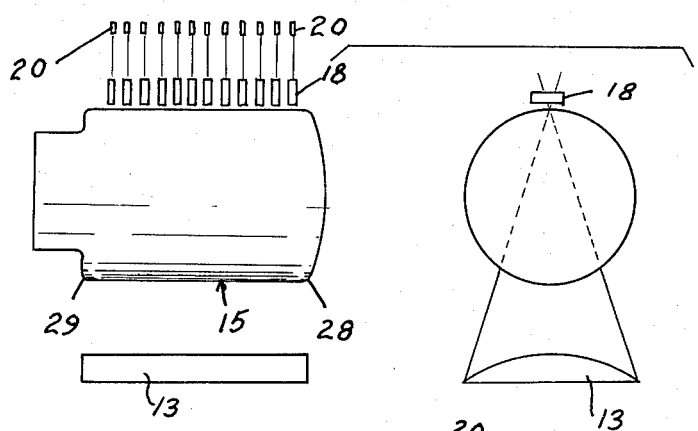
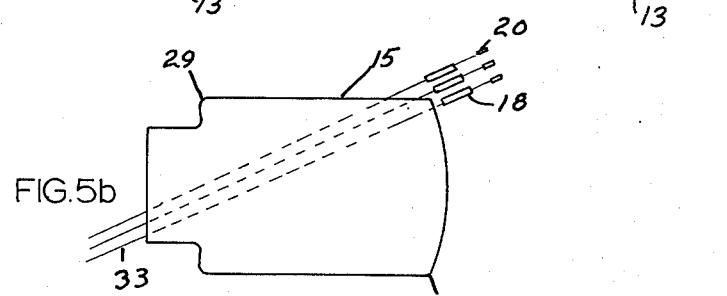
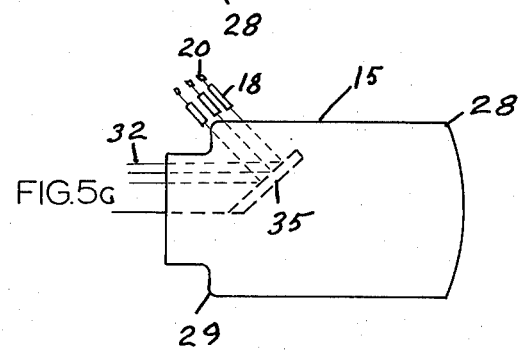
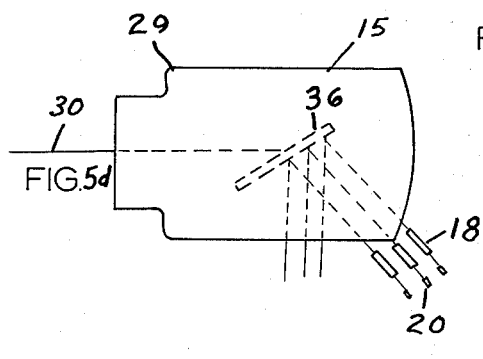
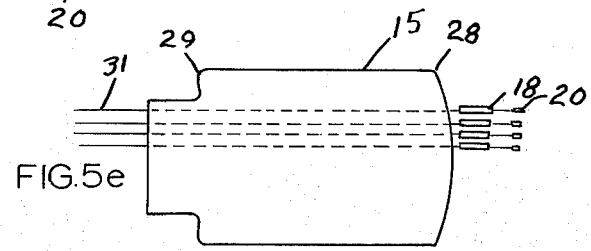
RICHARD D. BRUGGER

INSPECTION SYSTEM FOR REFLECTIVE AND TRANSPARENT ARTICLES

This is a continuation of application Ser. No. 213,999, filed Dec. 30, 1971, now abandoned.

BACKGROUND OF THE INVENTION

The system disclosed in the present application is a machine fed continuously with jars. The machine uses electro-optic means to detect foreign matter on the surface of the glass or on the glass surface of the jars and to reject the bad jars.

An "electric eye" is not satisfactory to inspect jars for foreign matter for two reasons: (1) the system looks for small dark spots on a proportionally large bright area. There are light sensors but not darkness sensors, so the proportional effect of a small dark spot in a bright field is indeed small and can be considered unmeasurable by any bulk light transmission measurement system; (2) the adverse optical properties of the jar are: (a) a jar is glass and reflects and refracts light; (b) the ridge molded into the bottom acts like a short focal length lens; (c) raised letters and numerals, logo, and other indicia act as light focusing and scattering means; (d) there are no plane surfaces in the basic jar structure; (e) four distinct regions must be examined: side, top shoulder, bottom shoulder, and bottom; (f) two seams created at mould parting lines extend down the sides and have optical properties that vary from jar to jar; and (g) the kick out plunger of the mold has scored a circular mark on the bottom of the jar.

GENERAL DESCRIPTION OF THE APPARATUS

An incandescent lamp filament is projected as a bar of light onto the jar by two cylindrical lenses arranged with their axis at right angles to each other. If it were not for the characteristics of the glass jar (such as the axial side ridge), a simple line of sensors with narrow receive apertures could do the detection. Because the ridge scatters the light, a wider aperture is necessary. If a narrow aperture were used, the electrical system could not determine whether the illuminance was down below the expected value because of doping on the glass or because of light scattering outside the aperture. It is necessary to make the distinction or, more properly, to identify the presence of doping and eliminate any effects of scattering by jar topology or inhomogenity (flaw or foreign matter in the glass). The word "on" is used herein to cover foreign matters or flaws both on the surface of the glass or within the glass itself.

The optical fibers capture the light scattered out to the side to the extent of the wide aperture. It is a fiber optic assembly that acts as a transition from rectangle to circular geometry, thus conforming the light area to the geometry of the photo transistor.

REFERENCE TO PREVIOUS PATENTS

In my previous U.S. Pat. No. 3,571,796, I disclose a rotation translation independent feature extraction means for electrically extracting optical information from an optically recognizable pattern regardless of the orientation of the pattern within the field of view which utilizes fiber optics to divide the image into a plurality of slices.

OBJECTS OF THE INVENTION

It is an object of the invention to provide an improved machine for inspecting glass containers.

Another object of the invention is to provide a method of inspecting glass containers, which is simple in construction, economical to manufacture, and simple and efficient to use.

Another object of the invention is to provide an improved system for inspecting jars.

With the above and other objects in view, the present invention consists of the combination and arrangement of parts hereinafter more fully described, illustrated in the accompanying drawings and more particularly pointed out in the appended claims, it being understood that changes may be made in the form, size, proportions, and minor details of construction without departing from the spirit or sacrificing any of the advantages of the invention.

GENERAL DESCRIPTION OF THE DRAWINGS

FIG. 5a shows one of the four inspection stations of the system according to the invention.

FIG. 5b shows a second of the four inspection stations.

FIG. 5c shows a third of the four inspection stations.

FIG. 5d shows an alternate of the second inspection station.

FIG. 5e shows a fourth of the four inspection stations.

DETAILED DESCRIPTION OF THE DRAWINGS

Figure 1:
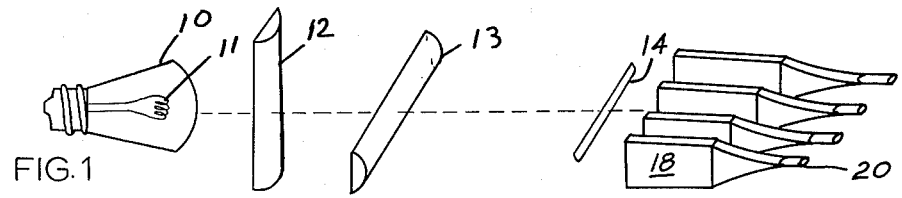
FIG. 1 is a diagrammatic view of a lamp filament projected as a bar of light onto a jar by a crossed-axis pair of cylindrical lenses.
Figure 1A:
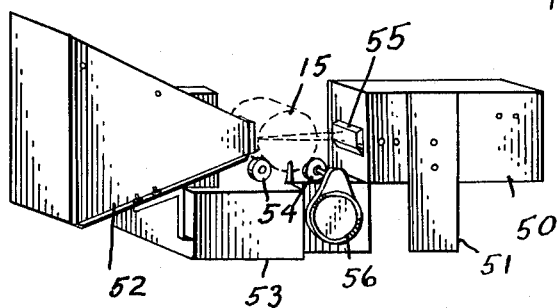
FIG. 1a shows a mechanical arrangement of the elements of the invention.

The apparatus utilized in the present application is shown in FIG. 1A. The light source is housed in the enclosure 50 which may be supported on bracket 51 on a suitable chassis. The envelopes 18, together with their associated electronic apparatus and circuitry, are housed in container 52. The baby food jar 15 being inspected is rotatably supported on rollers 54 that are driven by motor 56 to rotate the baby food jar in the beam of light emitting from the slot 55.

Figure 2:
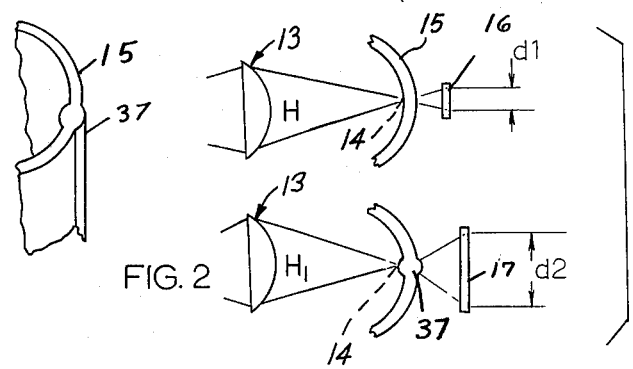
FIG. 2 shows a schematic diagram of a simple detection device that could be used for inspection of jars but for the axial ridges and other irregularities of the glass in the jar
Figure 3:
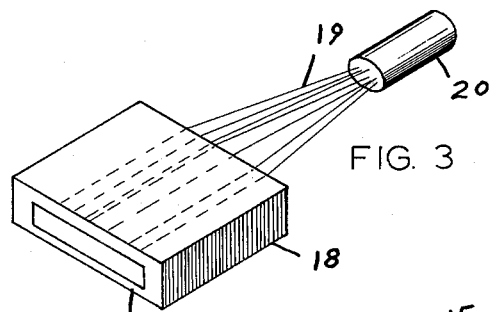
FIG. 3 shows an optical fiber bundle used to capture light scattered laterally and for converting the light to the geometrical shape of a phototransistor.
Figure 4:
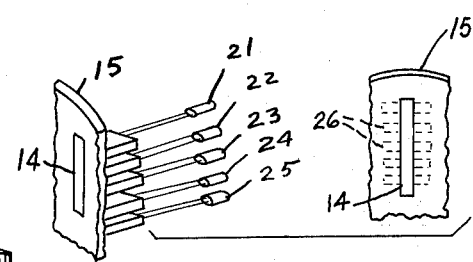
FIG. 4 shows a glass jar side configuration.

FIG. 1 shows the lamp 10 having a filament 11 that projects a bar of light through the cylindrical lens 12 and through the cylindrical lens 13 that is disposed at right angles to the lens 12. The bar of light 14 is projected onto a surface of the baby food jar 15. The baby food jar 15 may have a seam 37 formed by the parting line of the mold used to manufacture the jar. The light ray is projected through the jar 15 as indicated at H in FIG. 2 and it may be received in an aperture 16 and have a width d1. If the light H1 passes through a seam indicated at 37, the light is scattered, reflected and refracted and would require an aperture size 17 of width d2.

The light scattered at d2 can be impinged on the ends 26 of optical fibers 19 which are supported in an envelope of material 18, which may be a suitable plastic, and bundled into a bundle 20 and the light from the bundle may be impinged onto a photosensitive element. Elements 21, 22, 23, 24, and 25 are photo-sensitive electronic devices, the same as elements 10. Elements 35 and 36 are mirrors which reflect light onto the optical fiber bundle ends.

A plurality of these assemblies 18 may be supported adjacent the side of a jar, as indicated in FIG. 5a. The other assembly may be supported along the lower shoulder 28, another along the upper shoulder 29. A source of light similar to that shown in FIG. 1 may be directed through the jar as indicated in FIGS. 5a, 5b and 5e. The light may be reflected through the jars indicated in FIGS. 5d and 5c by use of a suitable mirror.

Figure 6:
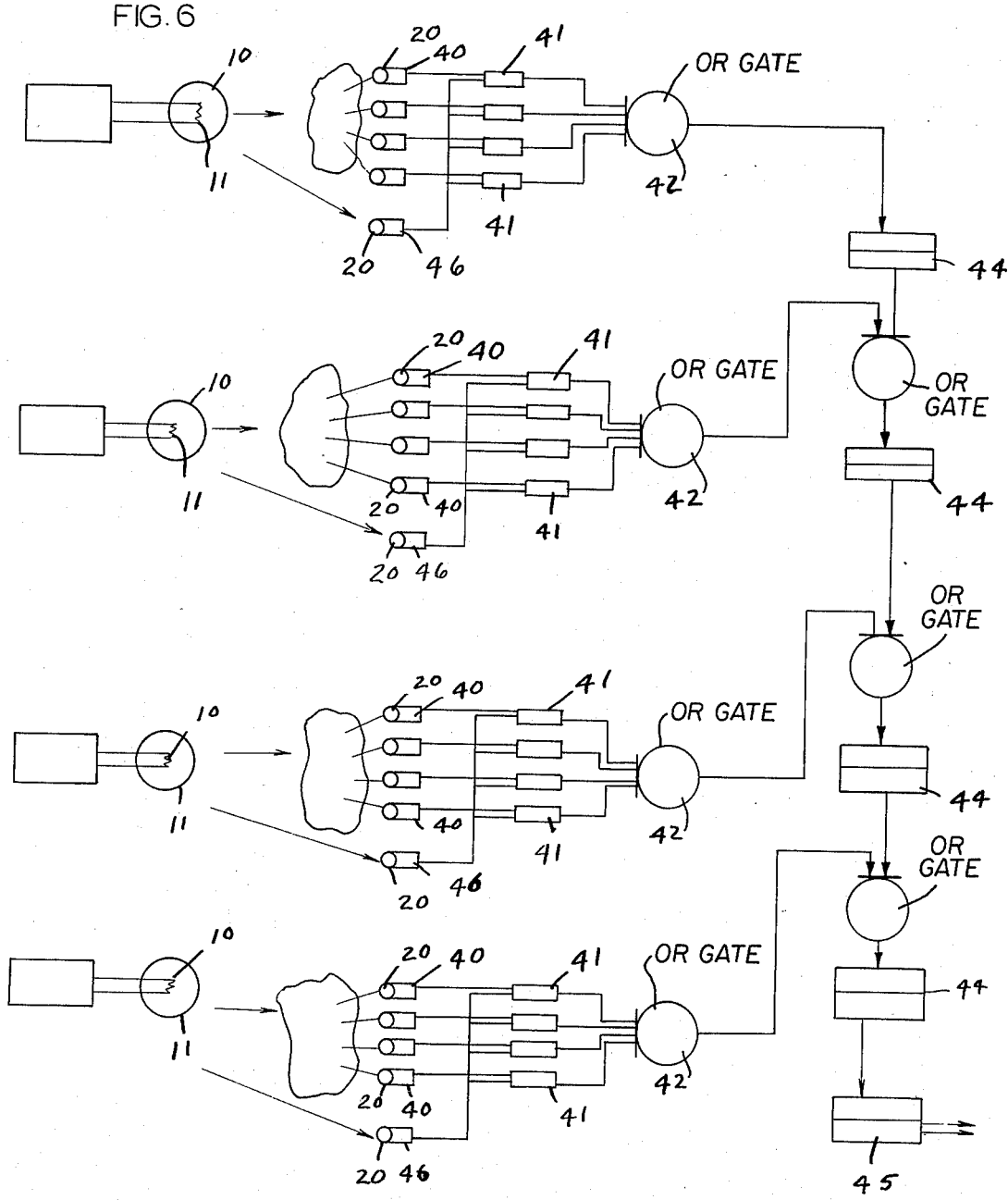
FIG. 6 shows a system of block diagram according to the invention.

The light from each of the bundles 20 may be connected to a suitable sensor 40 and thence into a threshold detector circuit 41 as shown in FIG. 6. The threshold detector circuit 41 can be connected through OR gates 42 and 43 and memory 44 to a suitable mechanism 45 for rejecting the baby food jars. Such mechanism and means of actuating is known in the art. The additional sensor 46 in each group provides a reference to set the threshold detector according to the prevailing light source intensity.

Where the illuminating beam must go through both sides of a jar, in FIG. 5a as an example, the beam is made considerably wider at the input side than at the exit side of the jar. The reason is that a marginal quality seam is then a small part of the area of the input beam width and will have little effect upon the light flux going to form a beam at the exit side. Minimizing effect of a seam at the exit side was discussed with the geometry of beam and fiber optics previously in this patent.

A mechanism for rotating the jars will be readily familiar to those skilled in the art and can be no more than a jar supported on rollers and rotated by a suitable electric motor.

The illustrated system contemplates inspecting the jars at a separate station for each of the FIGS. 5a–5e. It is understood that the four areas of the jar could be inspected at a single station by combining stations 5a–5e at a single station.

The foregoing specification sets forth the invention in its preferred practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A method of testing transparent articles to detect the presence of foreign substance thereon comprising,
   positioning said transparent article between a light source, capable of producing a focused bar of light on said article, and the input ends of a plurality of optical fiber elements having their input ends arranged in patterns having substantially the shape of said bar of light,
   focusing said bar of light onto said transparent article onto said input ends of said optical fiber elements arranged in the shape of rectangles having their major axis perpendicular to the major dimension of the bar of light for sensing light transmitted directly through said article and passing said light through said optical fiber elements, simultaneously onto a plurality of photo-sensitive elements.

2. A method of testing transparent articles to detect the presence of foreign opaque substances thereon recited in claim 1 wherein,
   said light source includes two cylindrical lenses disposed at right angles to each other focusing said bar of light on said object.

3. A method of testing transparent articles to detect the presence of foreign, opaque substances thereon recited in claim 2 wherein,
   said photo-electric devices are connected to OR circuits passing signals from said OR circuits to memory circuits and from said memory circuits to a suitable mechanism for accepting or rejecting said articles.

4. The method recited in claim 2 wherein said light is projected through said opening of said jar and thence through a lower shoulder of said jar and onto an optical fiber elements.

5. The method recited in claim 1 wherein said article is moved in relation to said light source and said sensing elements,
   and said light source is disposed on one side of said article and said photosensitive device is disposed on the opposite side of said article.

* * * * *